(12) United States Patent
Yeh et al.

(10) Patent No.: US 11,311,003 B2
(45) Date of Patent: Apr. 26, 2022

(54) MOBILE CULTURE ASSEMBLY FOR FEEDING LARVAE OF BLACK SOLDIER FLY

(71) Applicant: YU LAND BIOLOGICAL AGRICULTURE CO., LTD., Yuanlin (TW)

(72) Inventors: Ming-Chu Yeh, Taichung (TW); Wei-Hsuan Shen, Nantou County (TW)

(73) Assignee: Yu Land Biological Agriculture Co., Ltd., Yuanlin (TW)

(*) Notice: Subject to any disclaimer, the term of this patent is extended or adjusted under 35 U.S.C. 154(b) by 145 days.

(21) Appl. No.: 16/887,086

(22) Filed: May 29, 2020

(65) Prior Publication Data

US 2021/0368754 A1  Dec. 2, 2021

(51) Int. Cl.
*A01K 67/033* (2006.01)
*A01M 1/10* (2006.01)

(52) U.S. Cl.
CPC .......... *A01K 67/033* (2013.01); *A01M 1/106* (2013.01); *A01K 2227/706* (2013.01)

(58) Field of Classification Search
CPC .............. A01K 67/033; A01K 2227/706; A01M 1/106
See application file for complete search history.

(56) References Cited

U.S. PATENT DOCUMENTS

| | | | |
|---|---|---|---|
| 10,798,924 B1 * | 10/2020 | Massaro | A01K 67/033 |
| 2015/0296760 A1 * | 10/2015 | Perednia | A01K 67/033 119/6.5 |
| 2021/0137137 A1 * | 5/2021 | Leo | B01D 3/145 |

FOREIGN PATENT DOCUMENTS

| | | | |
|---|---|---|---|
| CN | 106106381 A | * | 11/2016 |
| CN | 110074066 A | * | 8/2019 |
| CN | 110250112 A | * | 9/2019 |
| CN | 111903620 A | * | 11/2020 |
| CN | 111903621 A | * | 11/2020 |
| CN | 111903622 A | * | 11/2020 |
| CN | 112197377 A | * | 1/2021 |
| CN | 112603184 A | * | 4/2021 |
| CN | 112715490 A | * | 4/2021 |
| CN | 112790162 A | * | 5/2021 |
| CN | 112868605 A | * | 6/2021 |
| CN | 112970628 A | * | 6/2021 |

(Continued)

*Primary Examiner* — Monica L Barlow
*Assistant Examiner* — Aaron M Rodziwicz
(74) *Attorney, Agent, or Firm* — Rosenberg, Klein & Lee

(57) ABSTRACT

A mobile culture assembly for feeding larvae of black soldier fly includes a mobile vehicle, a breeding device disposed in the mobile vehicle, and a turning device disposed on the breeding device. The breeding device includes spaced-apart breeding bodies, each of which defines a breeding space for accommodating feed materials and larvae. The turning device includes a base movably disposed on the breeding body, a feeding unit adapted to introduce the feed materials to the breeding space, a turning unit disposed under the base, a scrapping unit disposed at one end of the base, and a heat dissipating unit disposed on the base. The turning device serves to stir the feed materials and the larvae and also dissipate heat accumulated in the breeding space to thereby provide a preferable growing environment for the larvae, reduce feeding costs, and increase a reproductive rate and quality of the larvae effectively.

7 Claims, 8 Drawing Sheets

(56) References Cited

FOREIGN PATENT DOCUMENTS

| CN | 113142137 A | * | 7/2021 | |
|---|---|---|---|---|
| FR | 3070002 A1 | * | 2/2019 | ........... A01K 67/033 |
| KR | 102166308 B1 | * | 10/2020 | |
| WO | WO-2014171829 A1 | * | 10/2014 | ........... A01K 67/033 |
| WO | WO-2016011541 A1 | * | 1/2016 | ................ F21V 7/22 |
| WO | WO-2017007310 A1 | * | 1/2017 | ........... A01K 67/033 |
| WO | WO-2020225516 A1 | * | 11/2020 | ........... A01K 67/033 |
| WO | WO-2020246873 A1 | * | 12/2020 | ........... A01K 67/033 |
| WO | WO-2020246878 A1 | * | 12/2020 | ........... A01K 67/033 |
| WO | WO-2021099674 A1 | * | 5/2021 | ........... A01K 67/033 |
| WO | WO-2021133835 A1 | * | 7/2021 | ........... A01K 67/033 |

* cited by examiner

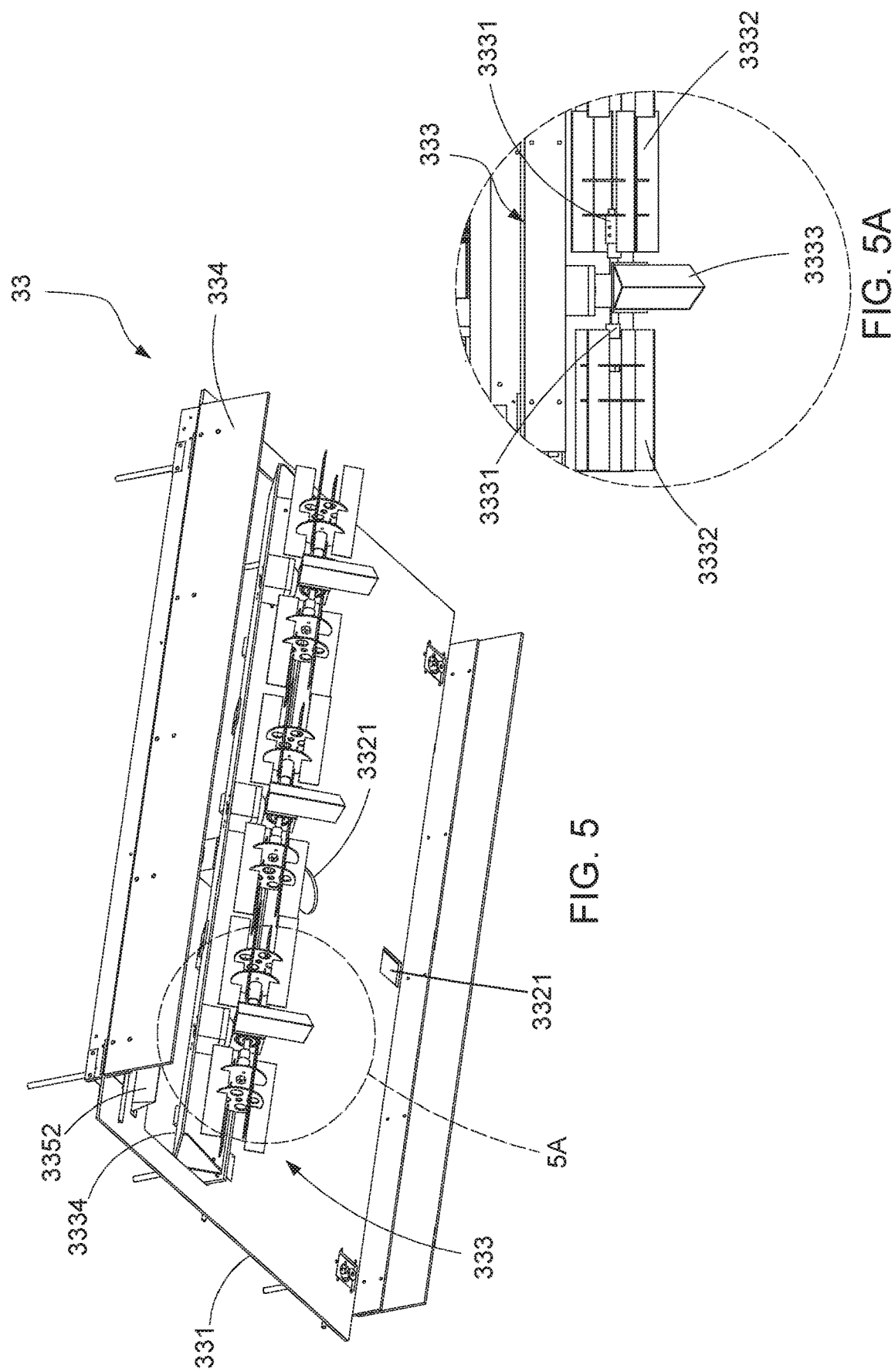

MOBILE CULTURE ASSEMBLY FOR FEEDING LARVAE OF BLACK SOLDIER FLY

BACKGROUND OF THIS INVENTION

1. Field of this Invention

This invention relates to a culture assembly and relates particularly to a mobile culture assembly for feeding larvae of black soldier fly.

2. Description of the Related Art

As the quality of life improves, innumerable waste has invisibly produced in our daily life, especially food waste. A great quantity of food waste produced from agriculture and cookery occupies 30% of domestic refuse. Meanwhile, the food waste has high water content and rich nutrition. Thus, the food waste will easily rot, attracts worms, and becomes smelly if it is not treated properly. Common methods for treating the food waste are landfill, compost and incineration. However, large area is required to execute the aforesaid methods and transportation costs are unduly high to result in low efficiency and a poor effect of resource recovery.

Thus, industry has introduced one kind of insects, namely black soldier fly, which can be fed by the food waste to thereby recycle and reduce the food waste. Black soldier fly is a special insect and considered as second helpful only to bee for human beings. During a growth stage of the black soldier fly, it will not harass human beings and animals, and will not damage crops. Especially, larvae of black soldier fly are saprophagous and can consume a large quantity of feed materials in a short time so that they can help reduce the food waste and livestock feces effectively. Meanwhile, the larvae can digest and decompose harmful germs in the livestock feces to thereby reduce environmental hazard. In addition, feces of the larvae are not smelly and can become organic fertilizer after being dried. Further, the larvae are considered as an excellent source of high quality protein owing to its high nutritive value. They can be made into feed materials for breeding chickens, ducks and fish. Thus, the black soldier fly has incomparable dominance than other insects and is beneficial for environment protection. However, a conventional culture assembly for feeding the larvae of black soldier fly is too simple and usually established at a fixed site. Food waste is continuously transported to the fixed site and filled into the culture assembly after being mixed with the larvae. However, the constant transportation of the food waste causes high transportation costs, and increases processing time and labor force. Moreover, all culture processes including refilling the feed materials, adjusting the temperature and the humidity of the culture assembly, removing feces of the larvae, and collecting imagoes of black soldier fly are executed manually, and that cost lots of labor force to manage and monitor the culture assembly. Furthermore, a large number of the larvae cluster together and rub against each other during the culture operation, and that will result in high heat. If the larvae are not stirred duly to release the heat, it will cause a high temperature of the culture assembly, and that will result in the mass mortality of the larvae owing to the high temperature. Thus, the breeding efficiency is reduced. Further, the breeding quality is difficult to control, and that requires to be improved.

SUMMARY OF THIS INVENTION

The object of this invention is to provide a mobile culture assembly for feeding larvae of black soldier fly attaining automation, reducing feeding costs, and increasing a reproductive rate and quality of the larvae.

The mobile culture assembly of this invention includes a mobile vehicle, a breeding device disposed in the mobile vehicle, and a turning device disposed on the breeding device. The mobile vehicle has a container enclosing an accommodation space, and a controller disposed on the container. The breeding device has a plurality of breeding bodies spaced from each other in the accommodation space, and a guiding unit disposed at two sides of each breeding body. Each breeding body defines a breeding space, and has an open end allowing the breeding space to communicate with the accommodation space. The turning device is electrically connected to the controller and has abase slidably disposed on the guiding unit, a feeding unit disposed on the base, a turning unit disposed under the base, a scraping unit disposed at one end of the base, and a heat dissipating unit disposed on the base and positioned relative to the turning unit. The turning unit has a driving rod, a plurality of stirring members and a plurality of pushing members respectively disposed on the driving rod. Thus, feed materials and larvae of black soldier fly are respectively filled in the breeding space, and simultaneously the controller drives the base to move along the guiding unit. Meanwhile, the controller actuates the turning unit and the scraping unit to stir the feed materials and the larvae, and actuates the heat dissipating unit to dissipate heat accumulated in the breeding space. After that, the feeding unit introduce the feed materials into the breeding space for breeding the larvae. Thus, a preferable growing environment for the larvae is provided. Mortality and feeding costs for breeding the larvae are reduced greatly. A reproductive rate and quality of the larvae are increased effectively.

Preferably, the mobile device has at least one detector disposed in the accommodation space of the container and a ventilating unit disposed on the container. The detector and the ventilating unit are electrically connected to the controller respectively. The detector serves to detect temperature and humidity of the accommodation space for obtaining detected data and transmit the detected data to the controller to thereby actuate the ventilating unit by the controller to execute air exchange.

Preferably, the turning unit has a baffle member disposed on the base to cover the driving rod, the stirring members, and the pushing members.

Preferably, the heat dissipating unit has a blower disposed on the base and an air guiding member connected to the blower and located at a place corresponding to the breeding space for delivering air generated by the blower to the breeding space.

Preferably, the turning device has a stop unit disposed at one side of each breeding body. The stop unit has a gate disposed at the open end and a power source electrically connected to the gate for carrying out an upward movement and a downward movement of the gate. The open end is open when the gate assumes the downward movement, and the open end is closed when the gate assumes the upward movement.

Preferably, the feeding unit has a feeding opening penetrating through the base and a feeding member connected to the feeding opening for mixing the feed materials. The feed materials are mixed by the feeding member and then introduced from the feeding opening into the breeding space.

BRIEF DESCRIPTION OF THE DRAWINGS

FIG. 5 is a bottom plan view showing the bottom of the turning device;

FIG. 5A is an enlarged view of the encircled portion 5A indicated in FIG. 5;

DETAILED DESCRIPTION OF THE PREFERRED EMBODIMENTS

Figure 1:
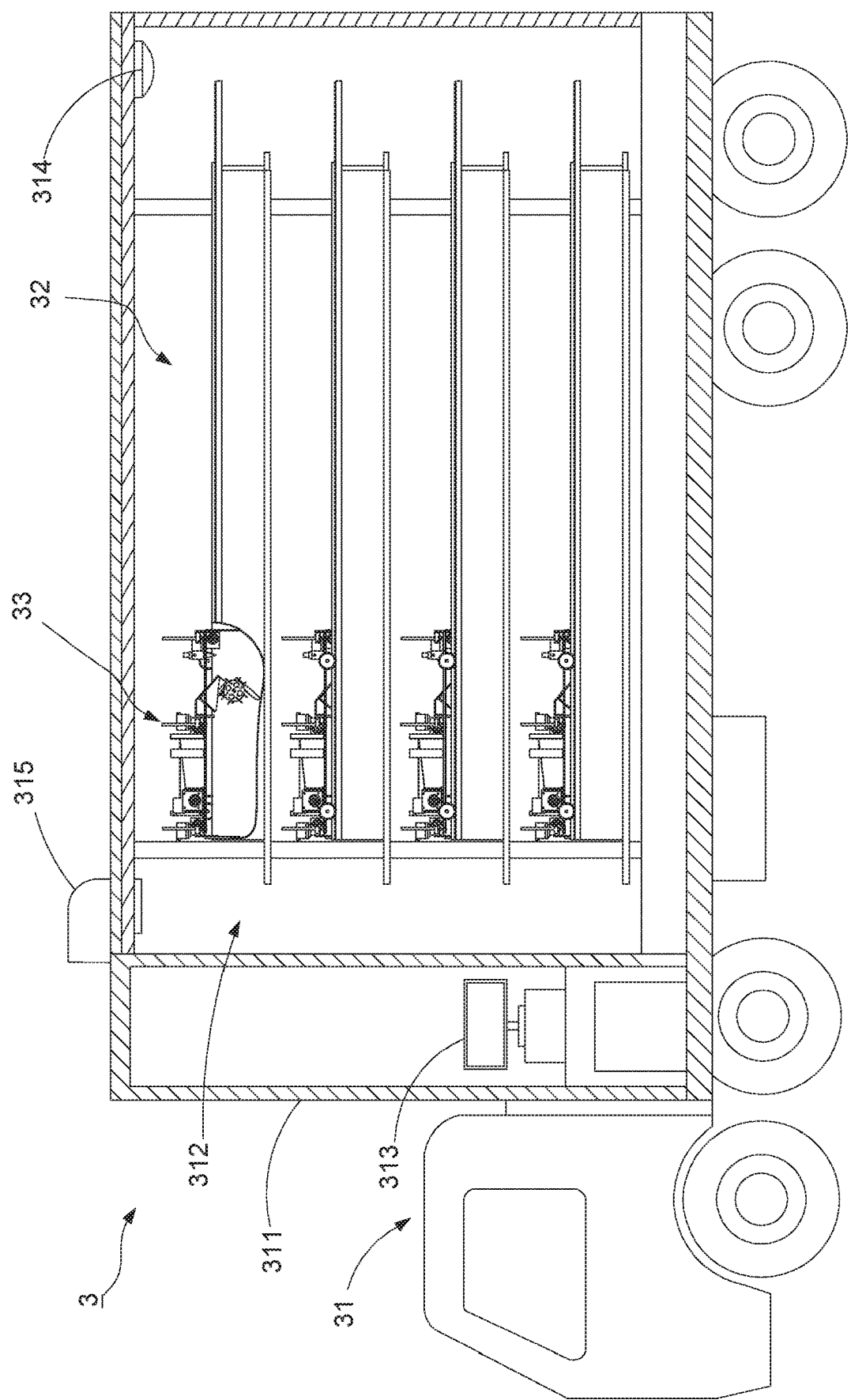
FIG. 1 is a schematic view showing a first preferred embodiment of this invention.
Figure 2:
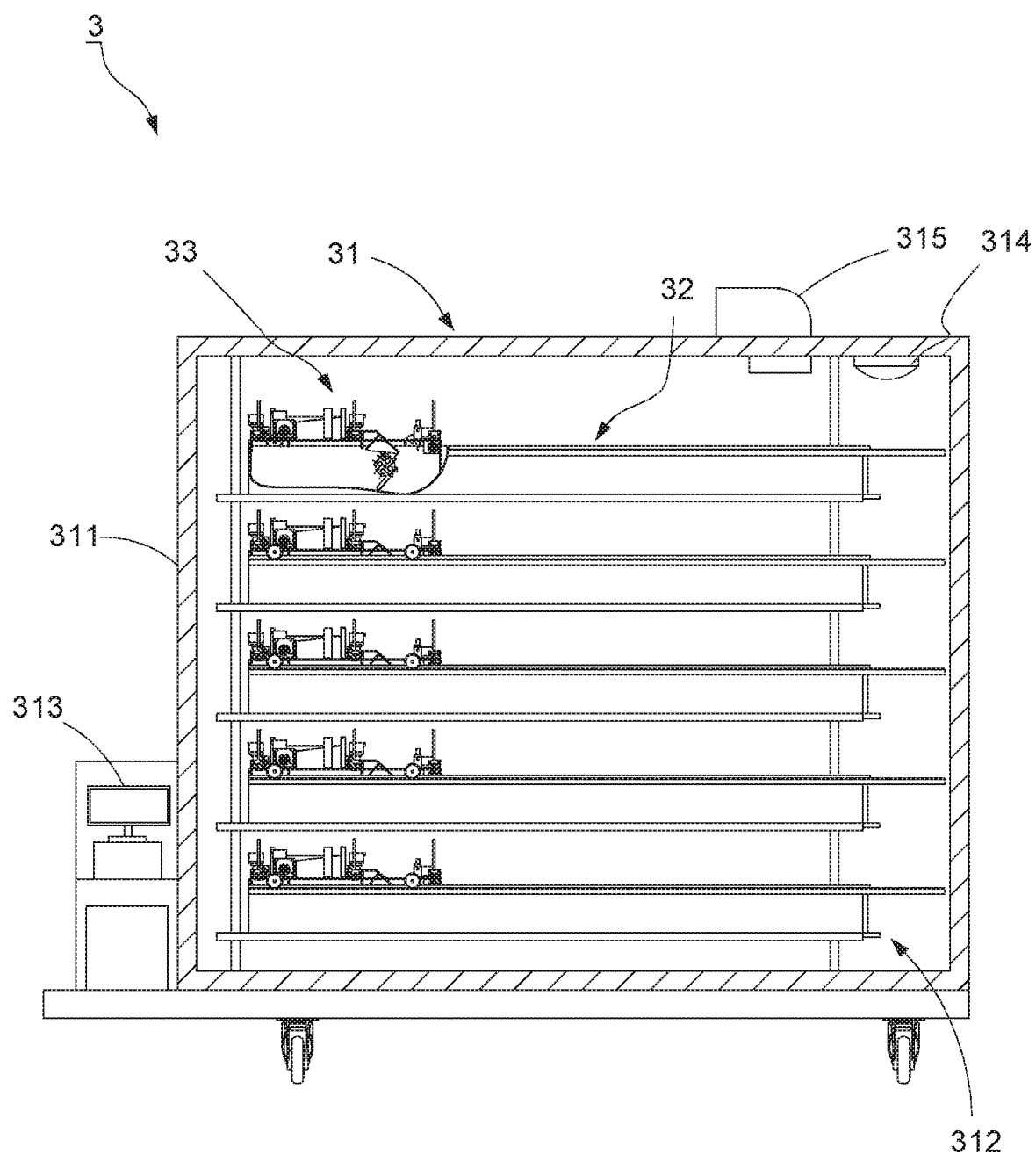
FIG. 2 is a schematic view showing a variation of the mobile vehicle.
Figure 3:
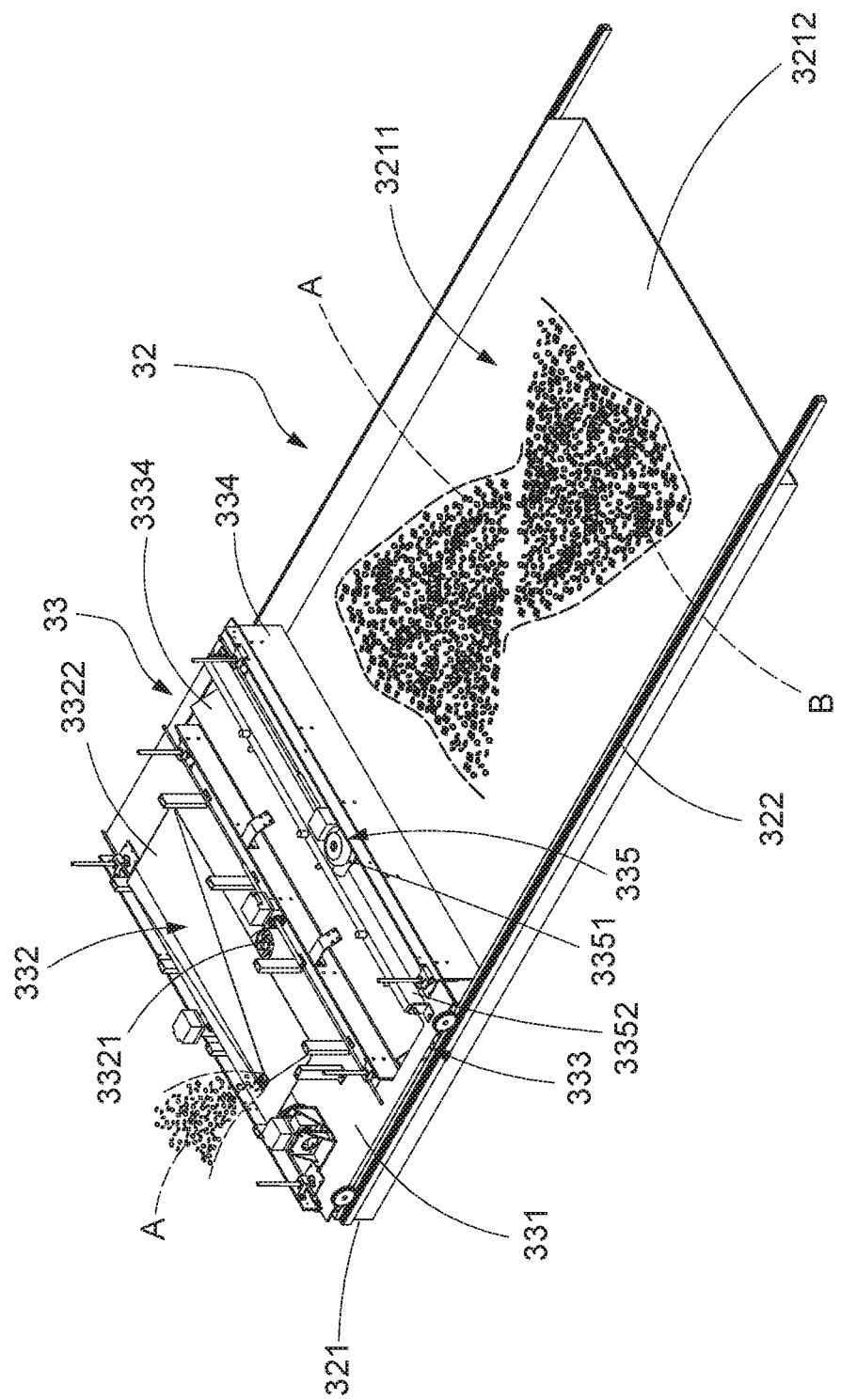
FIG. 3 is a perspective view showing the breeding device and the turning device.

Referring to FIG. 1 and FIG. 3, a mobile culture assembly 3 for feeding larvae B of black soldier fly of a first preferred embodiment of this invention includes a mobile vehicle 31, a breeding device 32 disposed in the mobile vehicle 31, and a turning device 33 disposed on the breeding device 32. The mobile vehicle 31 can be a container car capable of running anywhere according to needs, or a container provided with moving wheels thereunder as shown in FIG. 2. Here takes an example that the mobile vehicle 31 is a container car as shown in FIG. 1. The mobile vehicle 31 includes a container 311, an accommodation space 312 defined within the container 311, and a controller 313 disposed on the container 311. The mobile vehicle 31 has high mobility to thereby allow a user to drive and park the mobile vehicle 31 anywhere. Culture data including temperature and humidity preferable for breeding the larvae B are stored in the controller 313, and operation data for actuating the turning device 33 are also stored in the controller 313. In this preferred embodiment, at least one detector 314 is disposed in the accommodation space 312, and a ventilating unit 315 is disposed on the container 311 and controlled by the controller 313 to thereby circulate air around the accommodation space 312 and the outside. The detector 314 can be electrically connected to the controller 313 in a wireless way or in a wired way to detect temperature and humidity of the accommodation space 312 for obtaining detected data and transmit the detected data to the controller 313.

Referring to FIG. 1 and FIG. 3, the breeding device 32 is disposed in the accommodation space 312 of the container 311. The breeding device 32 has a plurality of breeding bodies 321 spaced from each other in the accommodation space 312, and a guiding unit 322 disposed at two sides of each breeding body 321. Each breeding body 321 defines a breeding space 3211 for accommodating feed materials A and larvae B of black soldier fly, and has an open end 3212 allowing the breeding space 3211 to be in open communication with the accommodation space 312.

Figure 4:
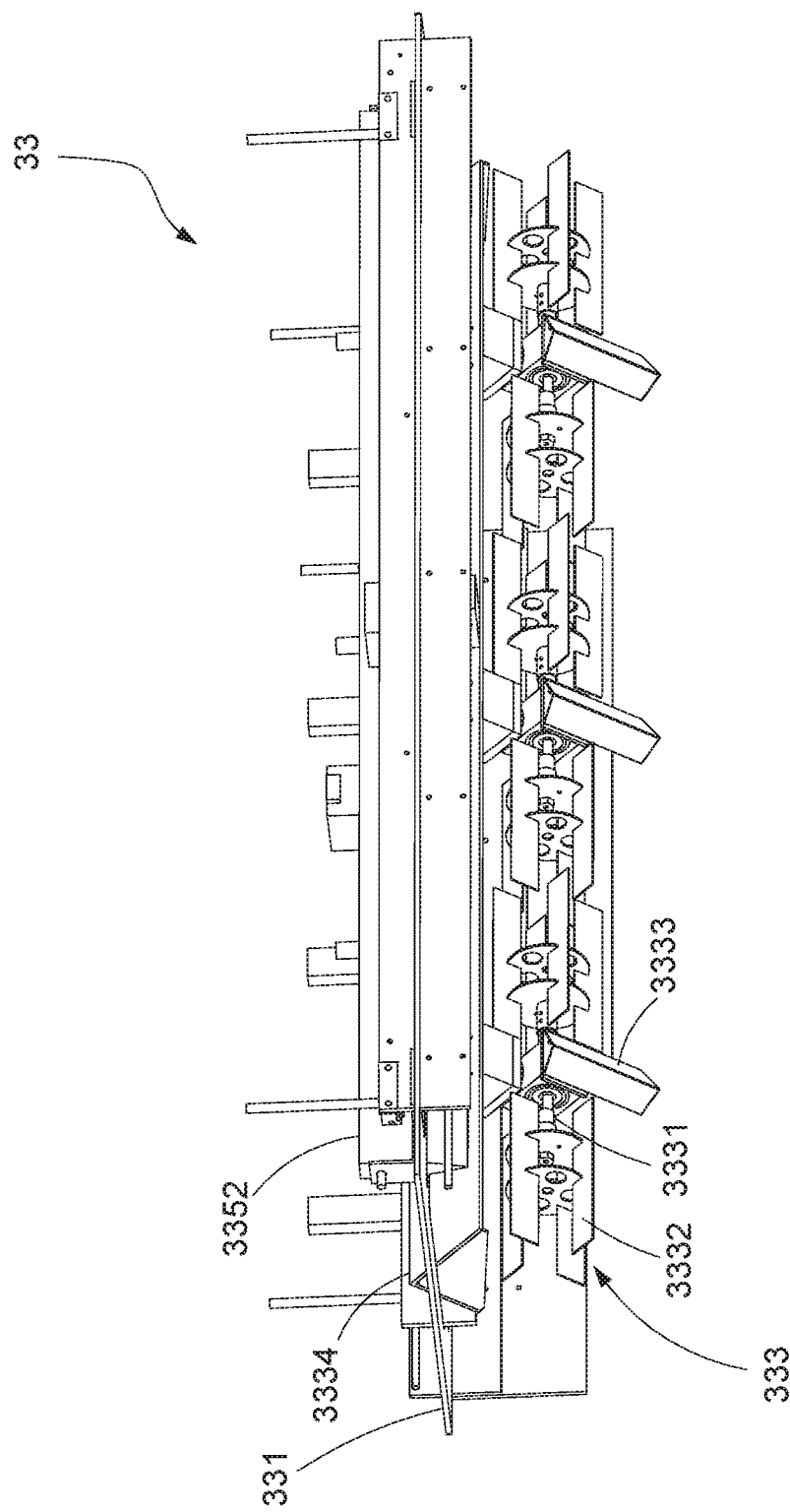
FIG. 4 is a perspective view showing the turning device.

The turning device 33 is disposed on each breeding body 321 and electrically connected to the controller 313. The turning device 33 has a base 331 movably disposed on the breeding body 321, a feeding unit 332 disposed on the base 331 for introducing the feed materials A into the breeding space 3211, a turning unit 333 disposed under the base 331 for stirring the feed materials A and the larvae B, a scraping unit 334 disposed at one end of the base 331, and a heat dissipating unit 335 disposed on the base 331 and located relative to the turning unit 333. The base 331 is capable of sliding along the guiding unit 322 for moving above the breeding space 3211. In this preferred embodiment, the feeding unit 332 has a feeding opening 3321 threading through the base 331, and a feeding member 3322 connected to the feeding opening 3321 for mixing the feed materials A and introducing the feed materials A into the breeding space 3211 through the feeding opening 3321. Referring to FIG. 3, FIG. 4 and FIG. 5, the turning unit 333 has a driving rod 3331, a plurality of stirring members 3332 disposed on the driving rod 3331, and a plurality of pushing members 3333 disposed on the driving rod 3331 and spaced from each other. Moreover, the turning unit 333 has a baffle member 3334 disposed on the base 331 to cover above the driving rod 3331, the stirring members 3332, and the pushing members 3333 to thereby prevent the feed materials A and the larvae B from being pushed toward the outside caused by the turning unit 333. Referring to FIG. 3, the heat dissipating unit 335 has a blower 3351 disposed on the base 331, and an air guiding member 3352 connected to the blower 3351 and situated at a place corresponding to the breeding space 3211 for delivering air generated by the blower 3351 to the breeding space 3211.

Referring to FIG. 1 and FIG. 3, a user can drive the mobile vehicle 31 to a place where a great quantity of food waste is placed. Meanwhile, an applied number of the mobile culture assembly 3 can be adjusted based on the quantity of the food waste to have one mobile culture assembly 3 or more than one mobile culture assembly 3. After that, the larvae B of black soldier fly and a proper quality of the feed materials A are introduced into the breeding space 3211 of each breeding body 321. In addition, the controller 313 actuates the turning unit 333 based on the operation data. The operation data including a stirring frequency and stirring time of the turning device 33 can be set based on requirements. Or, the turning device 33 also can be actuated irregularly by the controller 313. Since the larvae B can eat the feed materials A speedily and continuously, the feed materials A are consumed fast. Thus, the feed materials A can be filled in the feeding member 3322 in advance to allow the feed materials A to be introduced into the breeding space 3211 when the turning device 33 operates to thereby breed the larvae B.

Referring to FIG. 1, FIG. 5A, FIG. 6A and FIG. 6B, during the culture operation of the larvae B, the larvae B will cluster together and rub against each other to result in the increased temperature of the breeding space 3211. Meanwhile, the feed materials A in each breeding space 3211 contain moisture, and the moisture will increase the humidity of the breeding space 3211 if the feed materials A are not stirred duly. The unduly high temperature and humidity are bad for the larvae B and will increase the mortality of the larvae B. At this moment, the controller 313 carries out a rotation of the driving rod 3331 to simultaneously drive the stirring members 3332 to stir the feed materials A and the larvae B in the breeding space 3211, and the pushing members 3333 are also driven to push the feed materials A and the larvae B that are not stirred by the stirring members 3332. Simultaneously, the turning unit 333 can execute the stirring operation fully when the base 331 moves along the guiding unit 322 to the open end 3212 to thereby stir all feed materials A and larvae B in the breeding space 3211. In addition, the baffle member 3334 will block the stirred feed materials A and the stirred larvae B to prevent the stirred feed materials A and the stirred larvae B from being pushed toward the outside during the stirring operation. Moreover, the scraping unit 334 is moved with the base 331 to thereby scrape the feed materials A and the larvae B that are accommodated in the bottom of the breeding space 3211. Thus, the feed materials A and the larvae B located at different place of the breeding space 3211 can change the position duly and completely. Meanwhile, feces of the larvae B can be stirred to the bottom of the breeding space 3211. Hence, the hot and humid moisture will be released and the temperature will be reduced during the stirring operation. Further, during the stirring operation of the turning unit 333, the controller 313 will also drive the blower 3351 to send the air generated by the blower 3351 to the breeding space 3211 through the air guiding member 3352 to thereby dissipate the heat accumulated in the breeding space 3211 effectively.

Referring to FIG. 1 and FIG. 3, the detector 314 is applied to detect the temperature and the humidity of the accommodation space 312 to generate the detected data and send the detected data to the controller 313. The controller 313 will then compare the detected data with the culture data. If the detected data are in the range of the culture data, the controller 313 will not actuate the ventilating unit 315. When the moisture and the heat of the breeding space 3211 are discharged to the accommodation space 312 to increase the temperature and the humidity of the accommodation space 312, namely the detected data are over the range of the culture data, the controller 313 will actuate the ventilating unit 315 to discharge the air of the accommodation space 312 to the outside and introduce the outside air into the accommodation space 312 to thereby circulate the air around the accommodation space 312 and the outside. Hence, the temperature and the humidity of the accommodation space 312 are improved effectively.

Figure 6A:
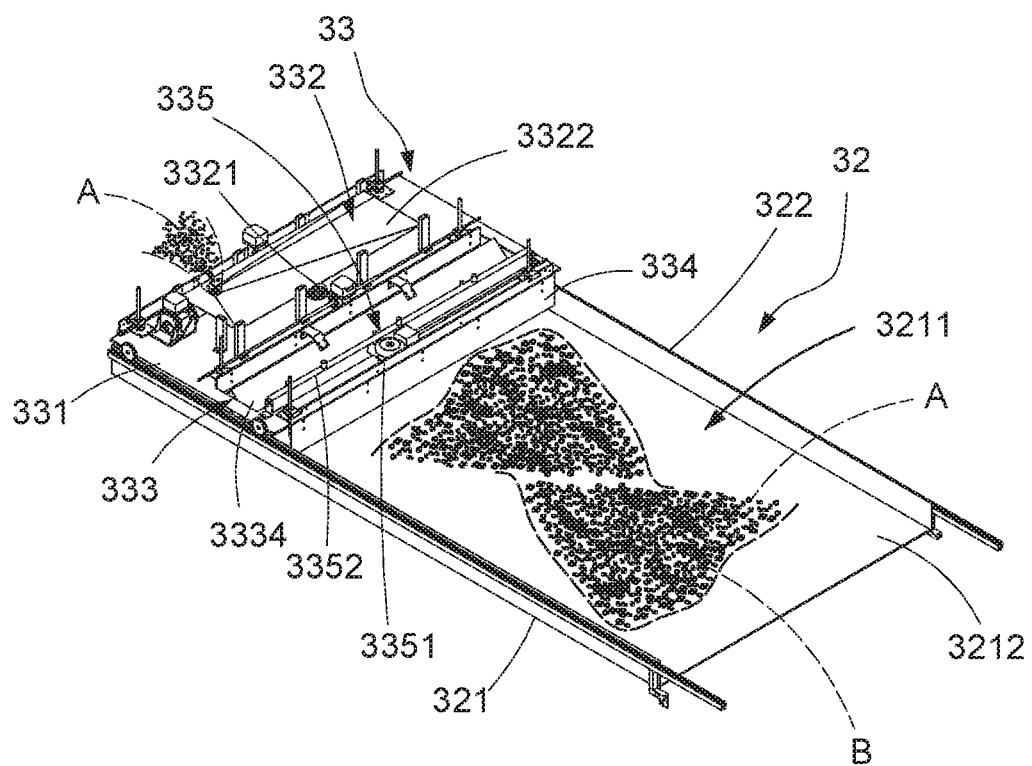
FIG. 6A and FIG. 6B are perspective views showing the operation of the turning device.
Figure 6B:
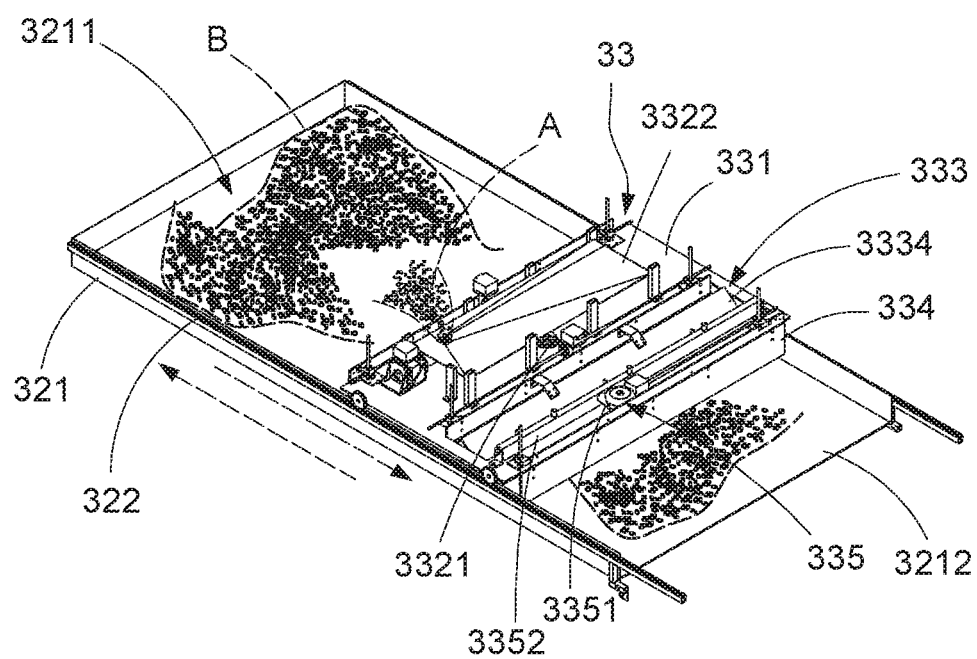

Referring to FIG. 1, FIG. 6A and FIG. 6B, during the stirring operation, the feeding member 3322 will mix the feed materials A which are filled in the feeding member 3322 in advance and introduce the feed materials A into the breeding space 3211 through the feeding opening 3321. Meanwhile, the stirring members 3332 and the pushing members 3333 will help mix the feed materials A together in the breeding space 3211 when executing the stirring operation. Hence, the mobile culture assembly 3 can attain the continuous culture operation of the larvae B of black soldier fly automatically without wasting much processing time and labor force to monitor and manage. Moreover, the mobile culture assembly 3 can be moved to anywhere easily, namely to the place where a great quantity of food waste is located to thereby breed the larvae B locally, reduce the transportation costs, and increase the breeding efficiency and the mobility. Furthermore, the temperature and the humidity of the breeding space 3211 and the accommodation space 312 can be adjusted automatically and effectively to thereby reduce the labor force, lower the feeding costs, and increase the reproductive rate and quality of the larvae B.

Figure 7:
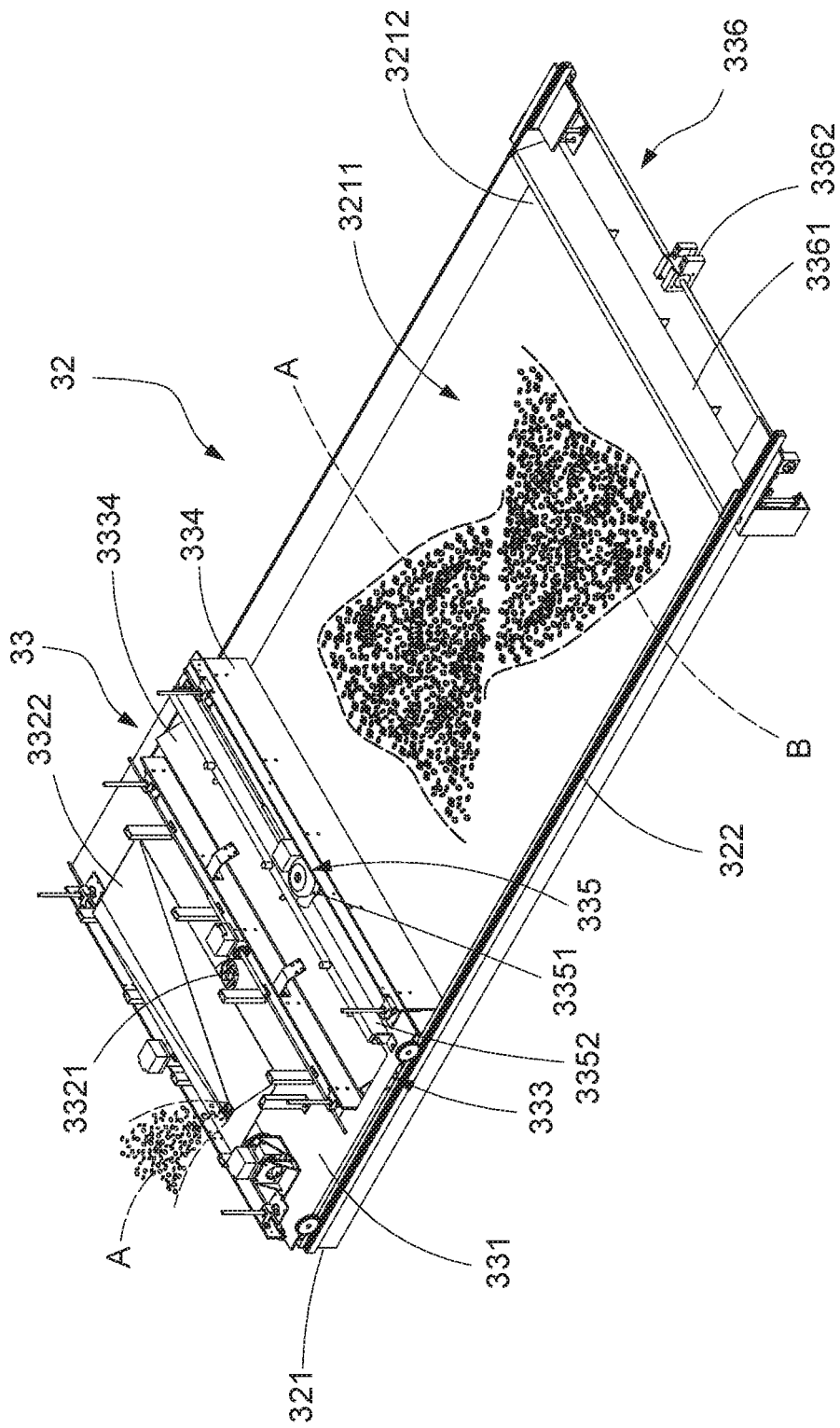
FIG. 7 is a perspective view showing a second preferred embodiment of this invention characterized by a stop unit.

Referring to FIG. 7 shows a second preferred embodiment of the mobile culture assembly 3 of this invention. The correlated elements and the concatenation of elements, the operation and objectives of the second preferred embodiment are the same as those of the first preferred embodiment. This embodiment is characterized in that the turning device 33 has a stop unit 336 disposed at one side of each breeding body 321. The stop unit 336 has a gate 3361 disposed at the open end 3212, and a power source 3362 electrically connected to the gate 3361 for controlling an upward movement and a downward movement of the gate 3361 whereby the open end 3212 is open when the gate 3361 assumes the downward movement and the open end 3212 is closed when the gate 3361 assumes the upward movement.

Figure 8:
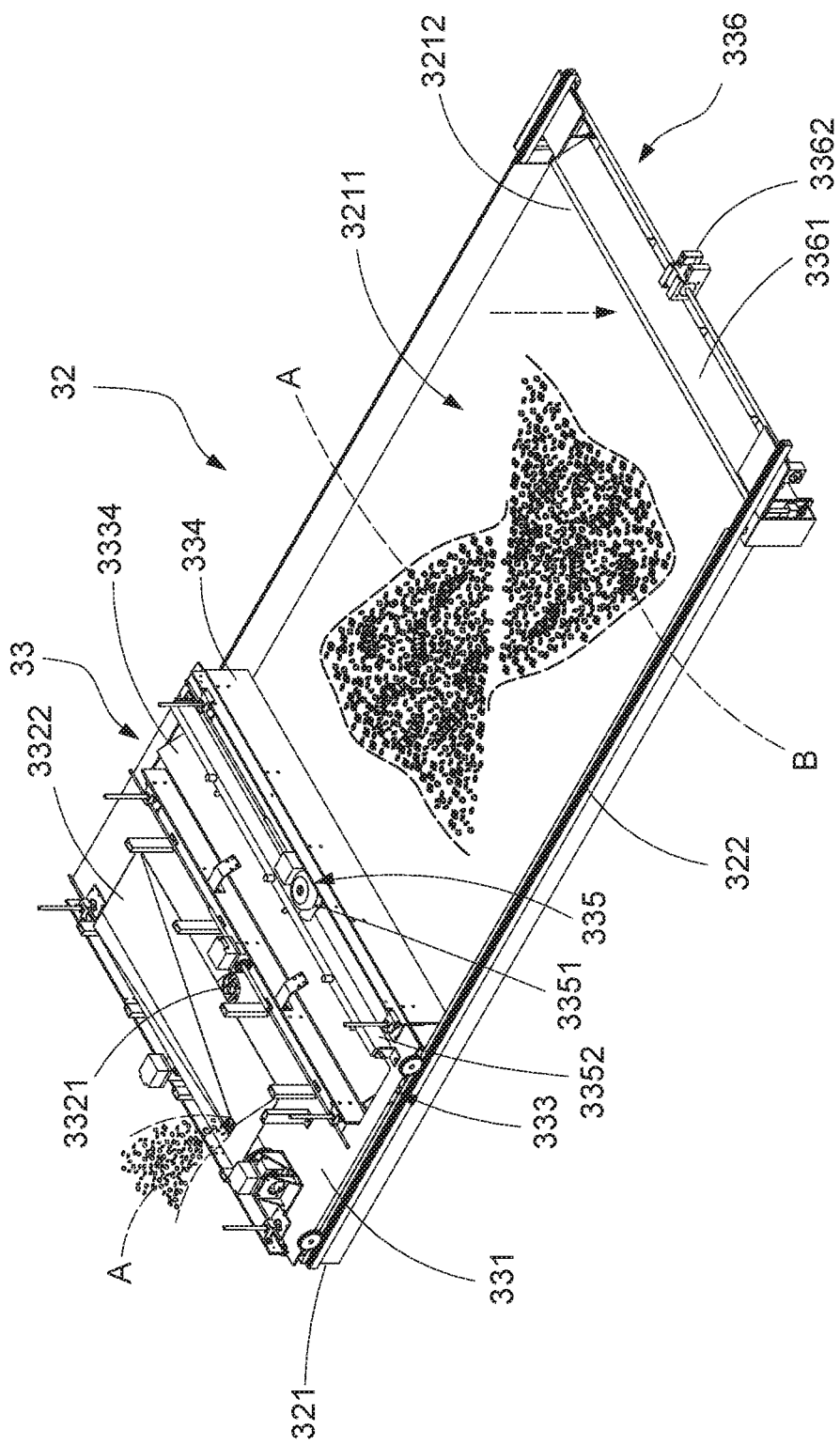
FIG. 8 is a perspective view showing the operation of the stop unit.

Referring to FIG. 7, when the gate 3361 assumes the upward movement to close the open end 3212, the gate 3361 can help keep the larvae B in the breeding space 3211 to thereby prevent the larvae B from dropping from the open end 3212. Referring to FIG. 8, when the base 331 moves to the open end 3212 to allow the turning unit 333 and the scraping unit 334 to stir and scrape the feed materials A and the larvae B that are placed near the open end 3212, the gate 3361 assumes the downward movement driven by the power source 3362 to open the open end 3212, namely to allow the breeding space 3211 to communicate with the accommodation space 312. The turning unit 333 and the scraping unit 334 then push the feces of the larvae B to the outside through the open end 3212. When the base 331 moves toward a direction opposite to the open end 3212, the gate 3361 is then driven by the power source 3362 to assume the upward movement to close the open end 3212. Thus, the cleaning operation of the breeding space 3211 can be executed effectively. The mortality and the feeding costs for breeding the larvae B are reduced greatly. The reproductive rate and quality of the larvae B are increased effectively.

To sum up, the mobile culture assembly of this invention takes advantages that the turning unit and the scraping unit to stir the feed materials and the larvae in the breeding space, the heat dissipating unit to dissipate the heat accumulated in the breeding space, and the feeding unit to introduce the feed materials into the breeding space to thereby attain automation, save the labor force effectively, provide the preferable growing environment for the larvae, reduce the mortality and the feeding costs for breeding the larvae, and increase the reproductive rate and quality of the larvae effectively.

While the embodiments of this invention are shown and described, it is understood that further variations and modifications may be made without departing from the scope of this invention.

What is claimed is:

1. A mobile culture assembly for feeding larvae of black soldier fly comprising:
    a mobile vehicle including a container, an accommodation space enclosed by said container, and a controller disposed on said container;
    a breeding device disposed in said container, said breeding device including a plurality of breeding bodies spaced from each other in said accommodation space of said container, and a guiding unit being disposed at two sides of each of said plurality of breeding bodies, each of said plurality of breeding bodies forming a breeding space to accommodate feed materials and larvae of black soldier fly and having an open end, said breeding space being in open communication with said accommodation space by said open end; and
    a turning device disposed on each of said plurality of breeding bodies and electrically connected to said controller, said turning device including a base movably installed on said breeding body, a feeding unit disposed on said base and adapted to introduce said feed materials into said breeding space, a turning unit disposed under said base for stirring said feed materials and said larvae of black soldier fly accommodated in said breeding space, a scraping unit disposed at one end of said base, and a heat dissipating unit disposed on said base and situated relative to said turning unit, said base being adapted to slide along said guiding unit for moving above said breeding space of said breeding body, said turning unit including a driving rod, a plurality of stirring members disposed on said driving rod, and a plurality of pushing members disposed on said driving rod and spaced from each other, said turning unit being actuated by said controller to stir said feed materials and said larvae of black soldier fly accommodated in said breeding space, and said heat dissipating unit thereby being actuated for dissipating heat accumulated in said breeding space.

2. The mobile culture assembly according to claim 1, wherein said mobile device includes at least one detector disposed in said accommodation space of said container and a ventilating unit disposed on said container, said at least one detector and said ventilating unit being electrically connected to said controller respectively, said at least one detector being adapted to detect temperature and humidity of said accommodation space for obtaining detected data and transmit said detected data to said controller, and said ventilating unit thereby being actuated by said controller to execute air exchange.

3. The mobile culture assembly according to claim 2, wherein said turning device includes a stop unit disposed at one side of each of said plurality of breeding bodies, said stop unit including a gate disposed at said open end and a power source electrically connected to said gate for controlling an upward movement and a downward movement of said gate, said open end being open when said gate assumes the downward movement, said open end being closed when said gate assumes the upward movement.

4. The mobile culture assembly according to claim 1, wherein said turning unit includes a baffle member disposed on said base to cover said driving rod, said plurality of stirring members, and said plurality of pushing members.

5. The mobile culture assembly according to claim 1, wherein said heat dissipating unit includes a blower disposed on said base and an air guiding member connected to said blower and located at a place corresponding to said breeding space for sending air generated by said blower to said breeding space.

6. The mobile culture assembly according to claim 1, wherein said turning device includes a stop unit disposed at one side of each of said plurality of breeding bodies, said stop unit including a gate disposed at said open end and a power source electrically connected to said gate for controlling an upward movement and a downward movement of said gate, said open end being open when said gate assumes the downward movement, said open end being closed when said gate assumes the upward movement.

7. The mobile culture assembly according to claim 1, wherein said feeding unit includes a feeding opening formed through said base and a feeding member connected to said feeding opening and adapted to mix said feed materials, said feed materials being mixed by said feeding member and then introduced from said feeding opening into said breeding space.

* * * * *